United States Patent [19]

Boyd et al.

[11] Patent Number: 4,736,396
[45] Date of Patent: Apr. 5, 1988

[54] TOMOSYNTHESIS USING HIGH SPEED CT SCANNING SYSTEM

[75] Inventors: Douglas P. Boyd, Woodside; Brian K. Rutt, San Francisco, both of Calif.

[73] Assignee: Imatron, Inc., South San Francisco, Calif.

[21] Appl. No.: 893,536

[22] Filed: Aug. 5, 1986

Related U.S. Application Data

[63] Continuation of Ser. No. 615,066, May 29, 1984.

[51] Int. Cl.$^4$ ............................................. G01N 23/03
[52] U.S. Cl. ......................................... 378/4; 378/10; 378/20; 378/901
[58] Field of Search ..................... 378/4, 10, 20, 901

[56] References Cited

U.S. PATENT DOCUMENTS

| | | | |
|---|---|---|---|
| 4,086,492 | 4/1978 | Lodge | 378/901 |
| 4,216,526 | 8/1980 | Karwowski | 378/901 |
| 4,352,021 | 9/1982 | Boyd | 378/137 |
| 4,411,012 | 10/1983 | Pfeiler | 378/4 |
| 4,439,866 | 3/1984 | Kato | 378/4 |
| 4,485,480 | 11/1984 | Kohno | 378/4 |
| 4,504,962 | 3/1985 | Moore | 378/10 |
| 4,573,179 | 2/1986 | Rutt | 378/20 |

OTHER PUBLICATIONS

Nishimura et al., "Digital Tomosynthesis Using a Scanned Projection Radiographic System", SPIE, vol. 314, Digital Radiography, (1981), pp. 31-36.

*Primary Examiner*—Janice A. Howell
*Assistant Examiner*—David P. Porta
*Attorney, Agent, or Firm*—Flehr, Hohach, Test, Albritton & Herbert

[57] ABSTRACT

A tomogram is obtained by tomosynthesis in a high speed CT scanning system in which fan beams of radiation are generated by sweeping an electron beam along a target, and collimated X-rays emitted by the target are received by an array of detectors after passing through a patient area between the target and array of detectors. The patient is moved through the collimated x-rays as the measurments are obtained, and the measurements are time-correlated to correspond to data measurements for a plurality of projection radiographs. The measurements for the plurality of radiographs are combined to tomosynthesize a tomogram at a selected plane in the patient.

4 Claims, 3 Drawing Sheets

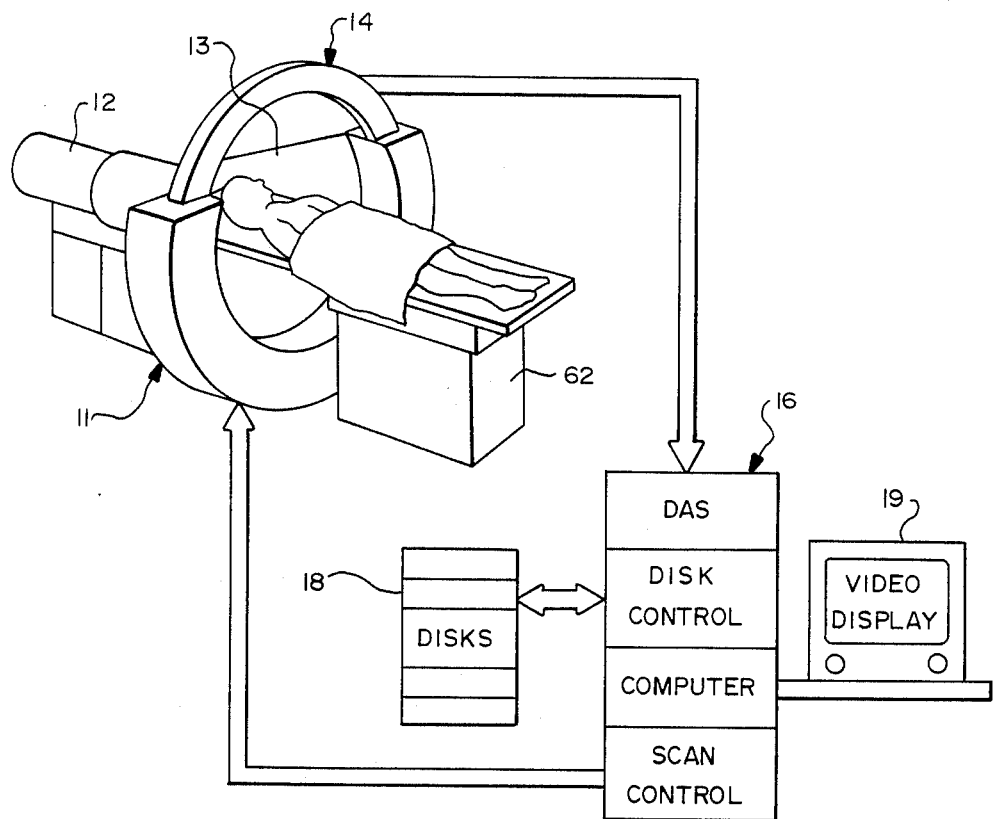
FIG.—1
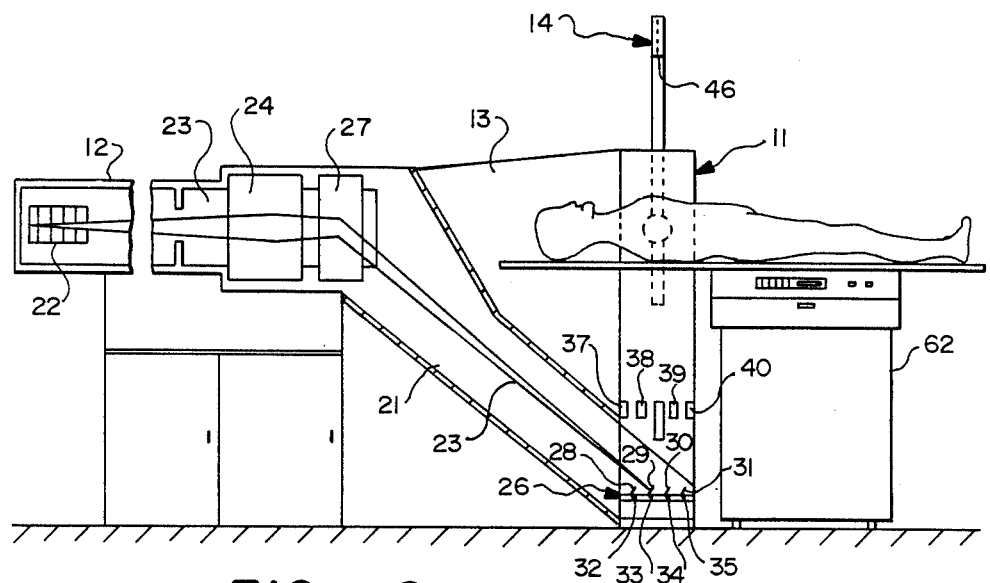
FIG.—2

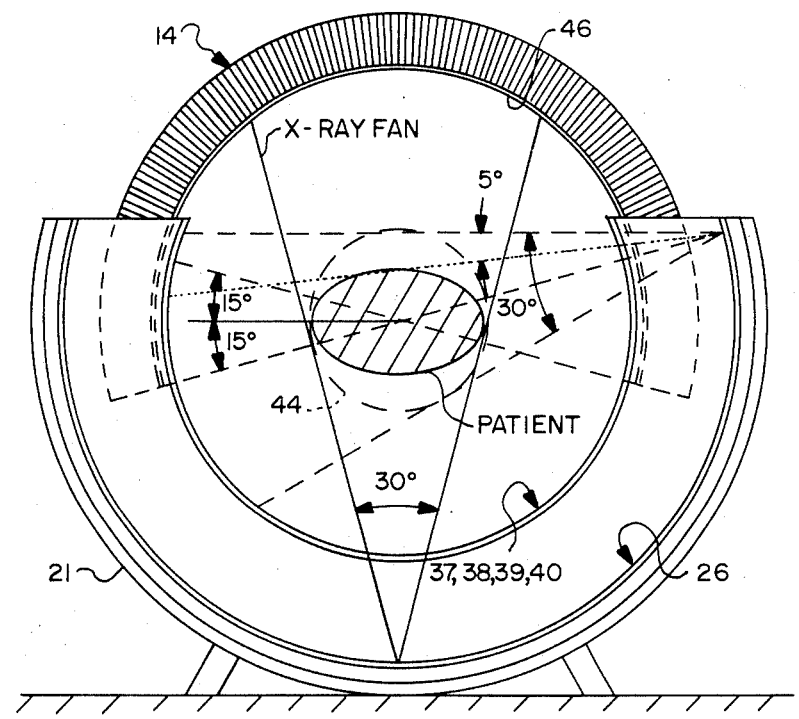
FIG.—3
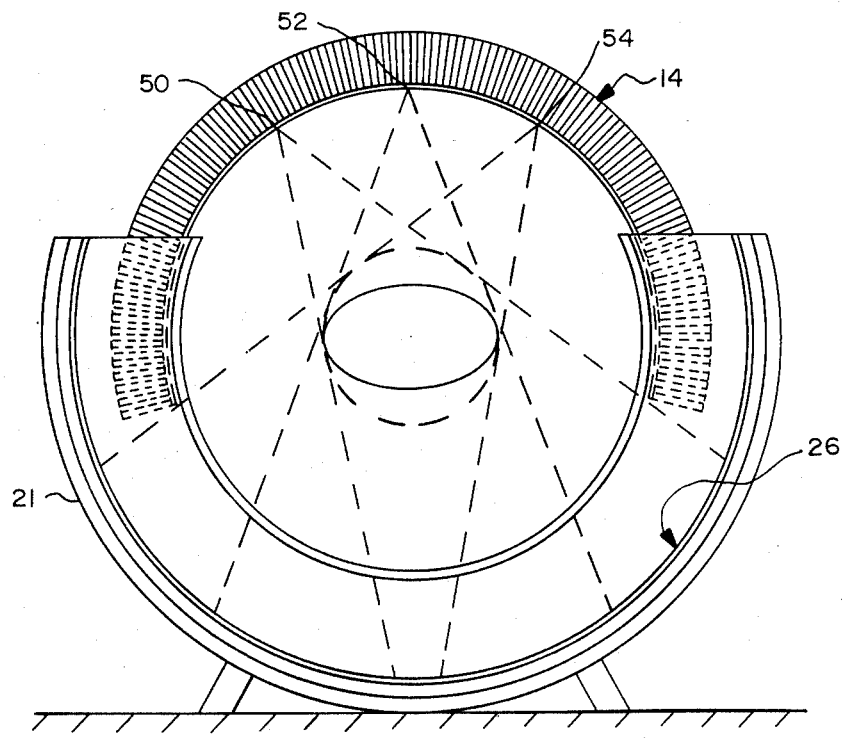
FIG.—4

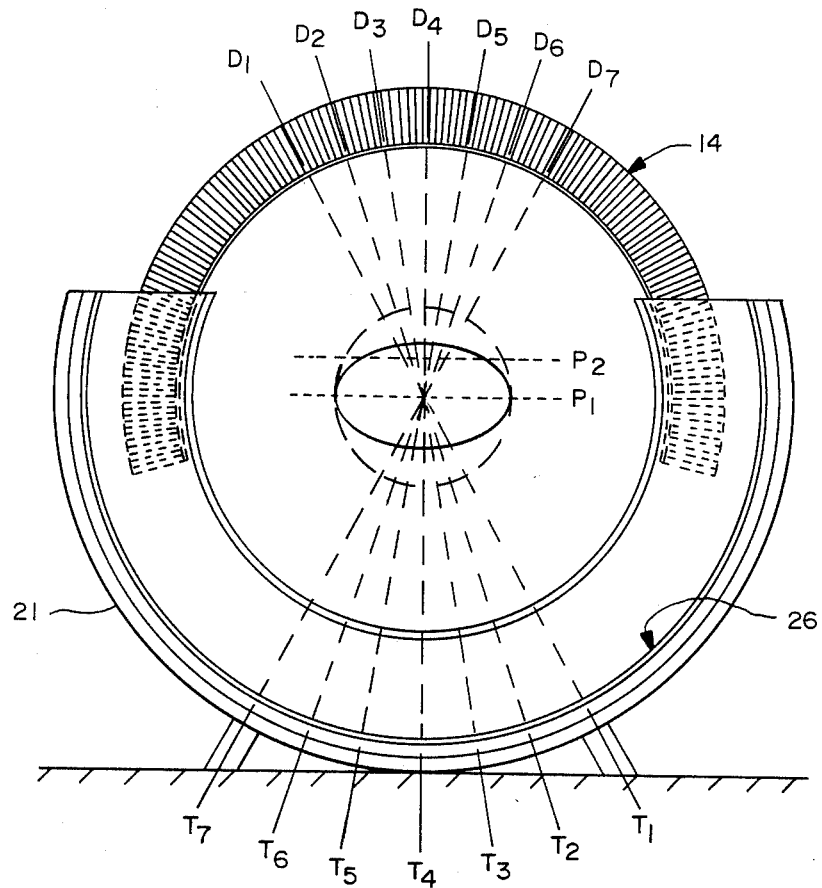
FIG.—5

TOMOSYNTHESIS USING HIGH SPEED CT SCANNING SYSTEM

This is a continuation of application Ser. No. 615,066 filed May 29, 1984.

This invention relates to radiographic imaging techniques, and more particularly the invention relates to tomosynthesis using a high speed computed tomography (CT) scanning system.

Tomosynthesis is a well-known technique for three dimensional imaging the basic principles of which were first formulated in the 1930's. See Grant "TOMOSYNTHESIS: A Three-Dimensional Radiographic Imaging Technique", IEEE—*Transactions on Biomedical Engineering*, Vol. BME-19, January 1972, pp. 20-28 and Nishimura et al, "Digital Tomosynthesis Using A Scanned Projection Radiographic System", SPIE, Vol. 314, *Digital Radiography*, pp. 31-36, 1981. In classical tomography, the X-ray source and detector move synchronously and continuously in opposite directions about a fulcrum residing in the plane of interest. The tomography procedure produces an image, or tomogram, of the desired plane by blurring the contributions from other planes. In tomosynthesis, a set of component radiographs is generated by pulsing the source at discrete intervals along the path used in classical tomography. The component images are superimposed and translated with respect to each other to synthesize a tomogram. The plane of focus is selectable as a function of translation distance. A single exposure sequence can produce many planes for viewing by varying the shifting and adding of the tomography data. Nishimura et al disclose digital tomosynthesis using a General Electric CT/T8800 system, which is a third generation CT scanner, operated in a scanned projection mode. Unfortunately, this technique is not practical because of the slow data acquisition speed due to the need for multiple patient couch translations.

The present invention is directed to a tomosynthesis technique which uses a high speed X-ray scanning system disclosed in U.S. Pat. No. 4,352,021 and commercially available from Imatron, Inc., assignee of the present application. In this system the X-ray source and the X-ray detectors are stationary and a plurality of fan beams of radiation is generated by sweeping an electron beam across a plurality of targets arcuately arranged whereby each target generates radiation fan beams.

The electronic scanning system incorporates a single electron beam tube. The electron beam is deflected by suitable magnetic and/or electric fields to produce a movable X-ray source on one of four adjacent semicircular target rings to provide scanning fan beams that can be used to image an entire volume of tissue in multiple sections. Such an electronic scanning system is vastly superior in speed to the mechanical scanning systems referenced above. Fraction-of-a-second scan time of a volume can be achieved as compared to one or more seconds required for the mechanical scan of a single section. The system eliminates the need for moving parts that require high precision end alignment. In addition, elaborate systems of sliding electrical contacts are eliminated. The scanner is an improvement over that shown and described in U.S. Pat. No. 4,158,142 in that it permits nearly simultaneous viewing multiple sections of the body which may encompass a region as large as the heart. The scanner can provide as many as weight sections.

The system employs a plurality of detectors mounted opposite the target rings. The detectors are arranged in two adjacent partial-circular ring arrays. Each of the arrays contains a multiplicity of detectors as for example, 432 detectors each, providing a total of 864 detectors. The angular separation of two adjacent detectors is in the order of 0.5 degrees resulting in very high resolution. The scanning system is provided with collimators both for the X-ray source and for the detectors. The source collimators comprise brass rings along with the detector housing which cooperatively define a plurality of fan beams. The detector collimators provide interchangeable options: dual section detector arrays, single section detector arrays and high resolution single section detector arrays. A variety of scanning modes can be selected with up to eight sections being scanned at a rate of at least one scan per second.

Data from more than two detectors are combined to produce images having tomographic blurring. A single couch translation is required. Further, because of the rapid acquisition of data for each image line, vessels and cardiac structures can be imaged without artifact.

Accordingly, an object of the invention is an improved method of tomosynthesis.

A feature of the invention is the use of a high speed CT scanner to obtain the tomosynthesis.

The invention and objects and features thereof will be more readily apparent from the following description and appended claims when taken with the drawing, in which:

FIG. 1 is a schematic diagram partly in perspective showing a computed tomographic X-ray transmission scanning system employing multiple electron beam targets.

FIG. 2 is a cross section view of the system of FIG. 1.

FIG. 3 is an end view of the system of FIG. 1.

FIGS. 4 and 5 are end views of the system of FIG. 1 illustrating tomosynthesis use thereof in obtaining three-dimensional projection data in accordance with the invention.

Referring now to FIG. 1, the system of U.S. Pat. No. 4,352,021 is seen to include three major components: a scan tube 11 including a cylindrical portion 12, and a semicircular conical portion 13; a detector array 14; and, a computer system 16. The scan tube projects an electron beam to target rings which generate X-rays. The X-rays are intercepted by the detector array 14. The output of the detector array is applied to the computer system 16. The computer system includes a plurality of storage discs 18 for recording the data for later processing. The computer system also includes an output which controls the scan tube. A video display 19 presents the data.

Referring more particularly to FIGS. 2 and 3, the scanning system and detection system are shown in more detail. The electron base tube 11 includes a vacuum envolope 21 which houses an electron gun 22 at the cylindrical end 12. The electron gun projects an axial electron beam 23 along the cylindrical portion. The focus coils 24 focus the beam onto targets 26. Bending coils 27 bend the beam so that it fans out along the partial-circular conical portion of the tube to impinge upon the partialcircular target rings. The target assembly 26 includes a plurality of partial-circular target rings 28, 29, 30 and 31. Suitable cooling coils 32, 33, 34 and 35 are associated with each of the target rings 28, 29, 30 and 31 respectively and serve to cool the target rings.

The bending magnets not only deflect the beam but rapidly sweep it along the partial-circular targets shown in FIGS. 2 and 3. The target rings are scanned serially to obtain a multiple section examination as will be presently described. Ring collimators 37, 38, 39 and 40 are disposed to intercept X-rays emitted by the target rings and define an X-ray beam projected as a one or two centimeter thick planar beam. A fan-shaped sector of this beam is detected by the curved detector array and the measured values are utilized to reconstruct a tomographic image.

The detector array is in the form of a ring which overlaps the ring collimators. In the overlapping region the detector fits between the second and third collimator rings 38 ad 39. The detector array 14 likewise may extend as much as 210° and is semicircular. A suitable detector collimator 46 serves to pass the X-rays to the associated detector. Overlap of the source and detector rings assures that at least 180° of projection data can be obtained.

The reconstruction region is indicated by the dotted circle 44, FIG. 3, and has a radius of approximately 50 centimeters. For oval-shaped patients such as indicated by the shaded region, more than 190° of projection data can be obtained. The degree of overscanning increases to about 230° for posterior regions. Overscan is known to be an important feature of CT scanning that can be used to reduce streak artifacts due to data inconsistencies at 0° and 180°. The rays that pass outside the reconstruction circle are used to calibrate the individual detectors in the stationanry array.

As disclosed in copending application Ser. No. 615,063 filed May 29, 1985 now U.S. Pat. No. 4,573,179 issued Feb. 25, 1986 for "Scanned Projection Radiography Using High Speed Computed Tomographic Scanning System", a projection radiograph is obtained with the described high speed scanner by using the output of a single detector position as the electron beam is swept along a single target track repeatedly and the patient is moved linearly past the collimated beam.

In accordance with the invention data is recorded by a plurality of the array of detectors as the electron beam is swept along the target, and the radiation measurements are time correlated to a plurality of X-ray emission sites along the detector array and thereby correspond to a plurality of projection radiographs. This is illustrated in FIG. 4 of the drawing in which fan beams of radiation, as defined at the detector sites 50, 52, 54, 62 are projected by the radiation source shown generally at 21 and thus correspond to data measurements for a plurality of projection radiographs. Using the known tomosynthesis techniques, the measurements at the plurality of detector sites are combined thereby producing images having tomographic blurring except at a plane within the patient which is determined by the selection of detector site measurements for combination. FIG. 5 illustrates the method of determining the plane of interest, P, by the spacing of the detectors, D, and the spacing of the target points, T. The illustrated spacing defines plane P1, whereas a closer spacing of the detectors or wider spacing of targets will define the plane P2. Thus, with a single scan of the electron beam along the target for each patient couch position, sufficient data is obtained to display tomograms at any arbitrary depth of focus using simple data processing methods.

In a preferred embodiment the projection data is acquired by approximately 50 detectors and is extracted for each patient couch position. The tomographic view created at an arbitrary depth is achieved by appropriately shifting and summing the data from all 50 detectors. The tomographic view is then displayed as a single line of a two dimensional tomographic image, and the procedure is repeated for each subsequent patient couch position. Since the data processing operation is a simple matter of shift and add, a complete two dimensional tomographic plane can be processed and displayed in approximately one second using the above-described high speed scanner and array processor.

Importantly, after data acquisition the tomographic plane can be chosen to represent arbitrary sagittal, coronal, or oblique planes at any desired depth in the patient volume. Accordingly, a patient is exposed to reduced radiation levels. This tomosynthetic capability provides enhanced diagnostic utility of the high speed scanner. Each detector position may comprise a single detector, or alternatively a plurality of adjacent detector measurements can be combined for use as the detector site signal.

While the invention has been described with reference to a specific embodiment, the description is illustrative of the invention and is not to be construed as limiting the invention. For example, the number and spacing of detector sites used to form the tomographic image will depend upon the depth of field and blurring to be achieved. Accordingly, various modifications and applications may occur to those skilled in the art without departing from the true spirit and scope of the invention as defined by the appended claims.

What is claimed is:

1. In a high-speed CT scanning system in which fan beams of radiation are generated by sweeping an electron beam along a target and collimated X-rays emitted by the target are received by an array of detectors after passing through a patient area between said target and said array of detectors, a method of obtaining a tomograph of a patient comprising the steps of sweeping said electron beam along said target, measuring radiation received at detector positions as said electron beam is swept along said target, said measured radiation being correlated in time to a plurality of X-ray target sites corresponding to a plurality of projection radiographs whereby a tomograph based on data for lines in a desired plane can be obtained and a tomograph based on data for lines in other planes will be blurred;

moving said patient past said collimated X-rays, said measured radiation being correlated in time to positions of said patient in said collimated X-rays, and combining measurements at said detector positions as correlated in time to positions of said patient and tomosynthesizing said tomograph from data for lines in said desired plane for said positions of said patient.

2. The method as defined by claim 1 wherein said step of measuring radiation received at detector positions includes measuring radiation with single detectors.

3. The method as defined by claim 1 wherein said step of measuring radiation at detector positions includes measuring radiation with a plurality of detectors and generating a single measurement using measurements from said plurality of detectors.

4. The method as defined by claim 1 wherein said step of combining measurements includes selecting particular detector positions to achieve a tomogram at a preselected plane in said patient.

* * * * *